United States Patent
Eom et al.

(10) Patent No.: US 7,253,326 B1
(45) Date of Patent: Aug. 7, 2007

(54) METHOD FOR PREPARING TRIMETHYLOLPROANE

(75) Inventors: Sung Shik Eom, Daejeon (KR); Dong Hyun Ko, Daejeon (KR); Ji Joong Moon, Daejeon (KR); Jae Hoon Choe, Daejeon (KR); Dae Sun Rew, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 11/401,429

(22) Filed: Apr. 10, 2006

(30) Foreign Application Priority Data

Mar. 7, 2006 (KR) .................... 10-2006-0021185

(51) Int. Cl.
*C07C 31/22* (2006.01)
*C07C 29/38* (2006.01)

(52) U.S. Cl. ..................... 568/853; 568/854

(58) Field of Classification Search ............. 568/853, 568/854

See application file for complete search history.

(56) References Cited

U.S. PATENT DOCUMENTS 3,183,274 A    5/1965   Robeson ................... 260/635
3,956,306 A    5/1976   Dawes et al. ........... 260/308 R
3,956,406 A *  5/1976   Palmer et al. ............... 568/854
4,594,461 A    6/1986   Merger et al. ............. 568/853

* cited by examiner

*Primary Examiner*—Elvis O. Price
(74) *Attorney, Agent, or Firm*—Cantor Colburn LLP

(57) ABSTRACT

The present invention relates to a method for preparing trimethylolpropane (TMP) comprising the steps of: 1) synthesizing trimethylolpropane by using n-butyl aldehyde, an aqueous solution of formaldehyde and an aqueous solution of alkali metal hydroxide through aldol condensation reaction and Cannizzaro reaction; 2) extracting trimethylolpropane from a resultant mixture of the step 1) by contacting the resultant mixture with an alcohol having 6 to 10 carbons; 3) removing alkali metal ion from a resultant extract of the step 2) by contacting the resultant extract with water; and 4) distilling the alkali metal ion-removed extract obtained from the step 3). According to the present invention, a separate formaldehyde recovery process can be omitted, the extraction efficiency of TMP can be maximized with using a relatively small amount of extraction solvent, the separation and recovery processes for extraction solvent can be simplified since a mixture of solvents is not used for TMP extraction, and the yield of TMP can be maximized while the amount of generated waste water can be minimized, thereby producing TMP economically with good efficiency.

17 Claims, 1 Drawing Sheet

METHOD FOR PREPARING TRIMETHYLOLPROANE

TECHNICAL FIELD

The present invention relates to a method for preparing trimethylolpropane (TMP). Specifically, the present invention relates to a method for preparing trimethylolpropane comprising the steps of: synthesizing trimethylolpropane from n-butyl aldehyde, an aqueous solution of formaldehyde, and an aqueous solution of alkali metal hydroxide through aldol condensation reaction and Cannizzaro reaction; extracting trimethylolpropane from the resultant mixture by using an alcohol having 6 to 10 carbons, preferably an alcohol having 8 carbons, and more preferably 2-ethylhexanol; removing alkali metal ion from the resultant extract by using water; and distilling the alkali metal ion-removed extract. According to the present invention, TMP can be prepared and extracted in good efficiency, with reducing the use amounts of solvent for extracting TMP and water for removing alkali metal ion, by separating the TMP extraction step and the alkali metal ion-removal step.

BACKGROUND ART

Trimethylolpropane (TMP) is a white crystalline material at room temperature, and widely used as starting material in various applications such as alkyd resin, saturated polyester, synthetic lubricant oil, polyurethane resin, plasticizer and the like. Accordingly, there have been continuous researches for economically producing TMP that is an industrially important source material.

TMP is synthesized from n-butyl aldehyde (n-BAL), formaldehyde, and alkali metal hydroxide through aldol condensation reaction and Cannizzaro reaction as represented by the following reaction schemes 1 and 2:

Reaction Scheme 1: Aldol condensation reaction

$CH_3CH_2CH_2CHO + 2HCHO \rightarrow CH_3CH_2C(CH_2OH)_2CHO$

Reaction Scheme 2: Cannizzaro reaction

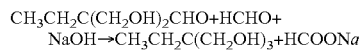
$CH_3CH_2C(CH_2OH)_2CHO + HCHO + NaOH \rightarrow CH_3CH_2C(CH_2OH)_3 + HCOONa$ U.S. Pat. No. 3,183,274 discloses a process for producing TMP wherein an excess amount of formaldehyde is used to increase the production yield, and a concentration step is incorporated before the extraction step to reduce the amount of extraction solvent. However, the '274 process requires an additional process for recovering formaldehyde remaining after the reaction since formaldehyde is excessively used to increase the production yield. Also, in the '274 process, a large amount of extraction solvent, about 7 times as much as the amount of raw material, is used to increase the TMP extraction efficiency from a mixture resulted from the synthesis reactions. Thus, the '274 process was disadvantageous in that the costs for facilities to recover the solvent are increased, whereby the investment costs and operational costs are increased. Further, in the '274 process, when extracting TMP by using organic solvent from a mixture resulted from the reaction despite using excessive amounts of formaldehyde and water, the resultant organic extract of TMP contains a considerable amount of sodium formate. Thus, this process has a problem that discoloration of TMP may be caused when the organic extract of TMP was distilled under vacuum.

Also, U.S. Pat. No. 3,956,306 discloses a method for separating TMP from a resultant reaction mixture by using two extraction solvents. However, the '306 method requires additional two separation steps for recovering the two extraction solvents used in the extraction step after the extraction is completed. Further, the amount of alkali metals present in the finally purified TMP is too high by about 42 ppm.

Moreover, U.S. Pat. No. 4,594,461 discloses a method for synthesizing TMP by synthesizing dimethylolbutanal as intermediate by using trialkylamine catalyst, and hydrogenating it by using Pb catalyst. However, the '461 method requires high temperature and high pressure, and thus the costs for facilities satisfying the reaction conditions are high. Further, the yield is decreased when amine is used as catalyst over a long period of time, and so periodic change of the catalyst is required to obtain an appropriately stable yield, whereby the cost for such change is additionally needed.

As described above, the conventional methods for producing TMP have used an excessive amount of starting material to increase the reaction yield, or tried to use various extraction solvents or conditions to separate TMP from alkali metal salt generated during the reaction. As a result, a considerable amount of TMP is lost during the extraction step, and the scale of facilities for extraction and recovery cannot but be increased due to the excessive use of extraction solvent, and thus the conventional methods have had limited commercial application. Further, in the conventional methods as described above, the amount of alkali metal remaining in the resultant even after the alkali metal salt-removing step is as considerably high as 40 ppm or more, and the remaining alkali metal may cause decomposition of TMP by high temperature during a subsequent vacuum distillation step for purifying TMP to highly purified product, resulting in discoloration of the final product.

DISCLOSURE OF THE INVENTION

The present invention is to solve the problems of the conventional methods as described above. Therefore, the object of the present invention is to provide a method for preparing purified TMP from the starting materials of n-butyl aldehyde, an aqueous solution of formaldehyde, and an aqueous solution of alkali metal hydroxide, in an effective and economical way without using many extraction solvents.

According to the present invention, the method for preparing trimethylolpropane comprises the steps of:

1) synthesizing trimethylolpropane by using n-butyl aldehyde, an aqueous solution of formaldehyde and an aqueous solution of alkali metal hydroxide through aldol condensation reaction and Cannizzaro reaction;

2) extracting trimethylolpropane from a resultant mixture of the step 1) by contacting the resultant mixture with an alcohol having 6 to 10 carbons;

3) removing alkali metal ion from a resultant extract of the step 2) by contacting the resultant extract with water; and 4) distilling the alkali metal ion-removed extract obtained from the step 3).

SYMBOLS SHOWN IN FIG. 1

Figure 1:
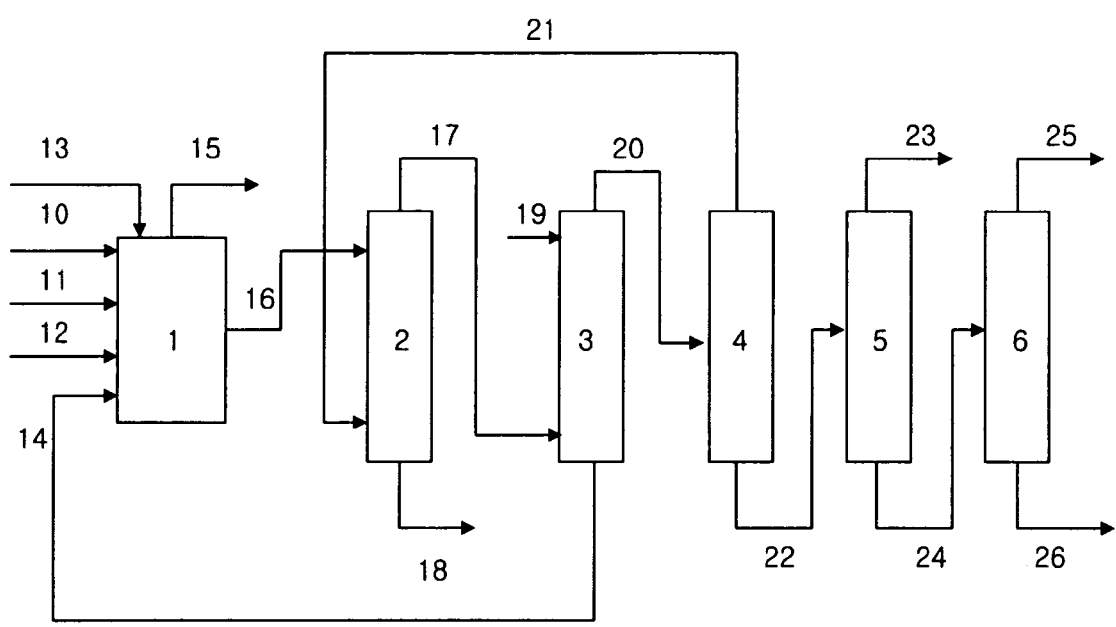
FIG. 1 represents a process diagram of an embodiment of apparatus and line construction for executing the method for preparing TMP according to the present invention.

1: Reactor
2: Multi-stage extractor
3: Multi-stage washing device
4: Distillation column for recovering solvent
5: Distillation column for removing lower boiling point material
6: Distillation column for removing higher boiling point material
10, 11, 12, 13, 14, 15, 16, 17, 18, 19, 20, 21, 22, 23, 24, 25 and 26: Line

BEST MODE FOR CARRYING OUT THE INVENTION

Each sub-step of the method for preparing TMP according to the present invention is described specifically below.

In the step 1) of the method according to the present invention, TMP is synthesized by using n-butyl aldehyde, an aqueous solution of formaldehyde and an aqueous solution of alkali metal hydroxide through aldol condensation reaction and Cannizzaro reaction. In this step, the n-butyl aldehyde, the aqueous solution of formaldehyde, and the aqueous solution of alkali metal hydroxide may be fed into a reactor in which condensation reaction and Cannizzaro reaction are conducted, at the same time, or some of them may be fed earlier. Only, to improve the reaction efficiency, it is preferable to feed the aqueous solution of formaldehyde earlier than the n-butyl aldehyde and the aqueous solution of alkali metal hydroxide, into the reactor. Also, in terms of reaction efficiency, it is preferable to feed the n-butyl aldehyde into the reactor for 70 to 120 minutes, and the aqueous solution of alkali metal hydroxide for 70 to 90 minutes.

Also, in the step 1), it is preferable to use 3 to 5 moles of formaldehyde in the formaldehyde aqueous solution to one mole of n-butyl aldehyde. Also, the synthesis of TMP is preferably conducted at 20 to 70° C. for 90 to 180 minutes. In the present invention, if the formaldehyde amount and the synthesis temperature and time in the step 1) are within the above preferred ranges, the synthesis of TMP can be optimized, and so no additional process for recovering formaldehyde is needed.

Further, in the step 1), lithium hydroxide, sodium hydroxide, potassium hydroxide or mixtures thereof may be used as the alkali metal hydroxide.

In the step 1) of the method according to the present invention, after completing aldol condensation reaction and Cannizzaro reaction in which n-butyl aldehyde, an aqueous solution of formaldehyde and an aqueous solution of alkali metal hydroxide are used as reactants, an organic acid such as formic acid is added to a resultant mixture to neutralize un-reacted reactants and control the pH within 5 to 7. After completing the neutralization, water in the resultant mixture is removed, for example, by vacuum distillation. In the vacuum distillation, the amount of water removed therefrom is preferably 65 to 75 parts by weight per 100 parts by weight of water present in the resultant mixture fed for the vacuum distillation, in terms of efficiency in the subsequent extraction and alkali metal removal steps. The above synthesis reactions, each sub-step for neutralization and concentration, may be conducted sequentially in a single reactor or each separate reactor step by step.

In the step 2) of the method according to the present invention, TMP is extracted from a resultant mixture of the step 1) by using an alcohol having 6 to 10 carbons, preferably an alcohol having 8 carbons, and more preferably 2-ethylhexanol, as extraction solvent. If the extraction solvent is an alcohol having less than 6 carbons or more than 10 carbons, the extraction efficiency is decreased. Further, in the step 2), the amount of the alcohol having 6 to 10 carbons is preferably 1 to 2 times the weight of the resultant mixture of the step 1), and the extraction of TMP is preferably conducted at 30 to 80° C. for 30 to 90 minutes. In the step 2) of the present invention, if the amount of alcohol having 6 to 10 carbons and the extraction temperature and time are within the above preferred ranges, the extraction of TMP is optimized, and so substantially 100% of TMP present in the resultant mixture of the step 1) can be recovered as organic layer, i.e. alcohol layer used as extraction solvent.

The extraction device used in the step 2) is not particularly limited, and thus a multi-stage extractor such as Scheibel-type of multi-stage extractor conventionally used for extraction of a specific target material using an extraction solvent in this field may be used.

In the step 3) of the method according to the present invention, alkali metal ion is removed from a resultant extract of the step 2) by using water. For the step 3) of the present invention, it is preferable to use deionized water, and the amount of used water is preferably 5 to 20 parts by weight to 100 parts by weight of the resultant extract of the step 2). Also, the removal of alkali metal ion is preferably conducted at 30 to 80° C. for 30 to 90 minutes. In the present invention, if the amount of used water and the temperature and time for the removal in the step 3) are within the above preferred ranges, the removal of alkali metal ion is optimized, and so the ion-removed extract obtained from the step 3) can contain alkali metal ions in 40 ppm or less, preferably 35 ppm or less, and more preferably 30 ppm or less.

The device used in the step 3) is not particularly limited, and thus a multi-stage washing device such as Scheibel-type of multi-stage washing device conventionally used in this field may be used.

According to a preferred embodiment of the present invention, the loss of TMP in the step 3) can be reduced by recycling the water used in the step 3) into a reactor conducting the step 1), and thus the TMP yield of the overall process can be increased.

In the step 4) of the method according to the present invention, purified TMP is produced by distilling the alkali metal ion-removed extract obtained from the step 3). According to a preferred embodiment of the present invention, in the step 4), the alcohol having 6 to 10 carbons which has been used as extraction solvent in the previous step 2) is distilled first and recovered or recycled into the step 2), and then lower boiling point material and higher boiling point material are removed sequentially by distillation to produce TMP with high purity. For the distillation of alcohol used as extraction solvent, a conventional multi-stage distillation apparatus such as 15-stage Oldershaw distillation apparatus may be used, and the condition for the distillation of alcohol may be varied depending on the types of alcohol and apparatus. Preferable conditions for the distillation may be a distillation column pressure of 200 to 250 mbar, a temperature of 130 to 180° C., and a reflux ratio of 0.1 to 1. After the distillation of alcohol used as extraction solvent, lower boiling point material and higher boiling point material are removed sequentially by using a conventional vacuum distillation apparatus. Here, the "lower boiling point material" refers to a material which has a lower boiling point than TMP among organic compounds excluding TMP, water, alcohol as extraction solvent, and alkali metal salt of formic acid, and the "higher boiling point material" refers to a material which has a higher boiling point than TMP among organic compounds excluding TMP, water, alcohol as extraction solvent, and alkali metal salt of formic acid. The conditions for distillation of lower boiling point material and higher boiling point material may be varied depending on the types of distilled material and distillation apparatus.

With reference to FIG. 1, the present invention is described more specifically below.

FIG. 1 is a process diagram for an embodiment of apparatus and line construction for executing the method for preparing TMP according to the present invention.

In FIG. 1, a formaldehyde aqueous solution, n-butyl aldehyde (n-BAL), and an aqueous solution of alkali metal hydroxide such as NaOH are fed into the reactor (1) through the three lines (10, 11 and 12), respectively. In a preferred embodiment, a certain amount of the formaldehyde aqueous solution is fed first into the reactor (1), and then the n-butyl aldehyde and the aqueous solution of alkali metal hydroxide are fed into the reactor (1) continuously for a certain period of time. Here, preferably, the amounts of formaldehyde and alkali metal hydroxide are 3 to 5 moles and 1 to 1.5 moles, respectively, to one mole of n-BAL. After completing the feeding, the reactions are conducted at 20 to 70° C. for 90 to 180 minutes to synthesize TMP. After completing the reactions, a certain amount of formic acid is fed into the reactor (1) through the line (13) to neutralize the resultant mixture to a level of pH 5 to 7. After completing the neutralization, the resultant mixture is distilled under vacuum to remove excessive water present therein through the line (15). At this time, if 65 to 75 parts by weight of water to 100 parts by weight of water present in the resultant mixture fed for the vacuum distillation is removed, a concentrated resultant mixture containing 40 to 50 weight % of TMP is obtained.

Next, the concentrated resultant mixture obtained above is fed continuously into the multi-stage extractor (2) for extracting TMP through the line (16). Meanwhile, as extraction solvent, an alcohol having 6 to 10 carbons, preferably an alcohol having 8 carbons, and more preferably 2-ethylhexanol, is fed into through the line (21) by 1 to 2 times the weight of the concentrated resultant mixture, and then TMP is extracted at 30 to 80° C. for 30 to 90 minutes. The resultant extract containing TMP is discharged from the multi-stage extractor (2) through the line (17).

Then, the TMP-containing resultant extract obtained above is fed continuously into the multi-stage washing device (3) through the line (17) while water for washing is fed into through the line (19) by 5 to 20 parts by weight of water to 100 parts by weight of the TMP-containing resultant extract. And, the resultant extract is washed at 30 to 80° C. for 30 to 90 minutes. The water used in the washing is discharged from the multi-stage washing device (3) through the line (14), thereby removing alkali metal salt contained in the TMP-containing extract. The water discharged through the line (14) is recycled into the reactor (1) to minimize the loss of TMP.

Next, the TMP-containing extract obtained by washing and removing alkali metal ion is fed into the distillation column (4) for recovering solvent through the line (20). In the distillation column (4), the alcohol used as extraction solvent is distilled and recovered, and the recovered alcohol is recycled into the multi-stage extractor (2) through the line (21) to minimize loss of the extraction solvent. Then, the TMP-containing resultant extract which is obtained by the distillation of the extraction solvent is fed sequentially into the distillation columns (5) and (6) which use vacuum distillation conventionally known in the art, thereby removing sequentially lower boiling point material and higher boiling point material present in the extract together with TMP. Finally, TMP product with high purity is discharged through the line (25), and other residues are discharged through the line (26).

As described above, in the present invention, a separate formaldehyde recovery process may be omitted by optimizing the use amount of formaldehyde and the reaction conditions for TMP synthesis. Also, the present invention can maximize the TMP extraction efficiency by selecting optimum extraction solvent and extraction conditions, with using relatively a small amount of extraction solvent. Further, in the present invention, the separation and recovery processes for extraction solvent can be simplified since a mixture of solvents is not used for TMP extraction. Also, the yield of TMP can be maximized, and the amount of waste water generated therein can be minimized, by recycling the water used in the washing into reactors.

The present invention can be more specifically explained by the following examples. However, it should be understood that the present invention is not limited by these examples in any manner.

EXAMPLE 1

1) Synthesis of TMP and Concentration of the Resultant Mixture 390.6 g (4.8 mol) of formaldehyde and 719.2 g of deionized water were fed into a 2 L reactor. Then, into the reactor, 108.2 g (1.5 mol) of n-butylaldehyde (n-BAL) and 132.5 g of 48% aqueous solution of sodium hydroxide (1.6 mol of sodium hydroxide) were fed and reacted continuously for 90 minutes and 75 minutes, respectively. The reactor temperature at the time of feeding the reactants was maintained at 45° C. After completing the feeding, the reactor temperature was elevated to 50° C., and the synthesis was further conducted for 30 minutes. After the further synthesis for 30 minutes, the resultant mixture contained 182.2 g (1.4 mol) of TMP, which is an amount corresponding to 13.5 parts by weight to 100 parts by weight of the resultant mixture.

The resultant mixture was fed with 7.7 g of formic acid for neutralization, and distilled under vacuum. Then, water was removed through the top of the reactor to obtain 304.8 g of concentrated resultant mixture. The resultant mixture and the concentrated resultant mixture were analyzed by using Gas Chromatography. The analysis results are shown in Table 1 below.

TABLE 1

| Composition | Resultant mixture | (parts by weight) Concentrated resultant mixture |
|---|---|---|
| Water | 76.8 | 26.1 |
| TMP | 13.5 | 44.9 |
| Lower boiling point material | 0.5 | 1.7 |
| Higher boiling point material | 2.0 | 3.3 |
| Sodium formate | 7.2 | 24.0 |

2) Extraction of TMP

The concentrated resultant mixture obtained from the step 1) was fed into the top of a 7 L Scheibel-type multi-stage extractor at the rate of 40 g/min while 2-ethylhexanol as extraction solvent was fed continuously into the bottom of the multi-stage extractor at the rate of 60 g/min, thereby extracting TMP. The extraction temperature was 60° C. As a resultant extract, TMP-containing 2-ethylhexanol solution was obtained through the top of the multi-stage extractor at the rate of 83.3 g/min. There was no loss of TMP during the extraction (100% of extraction efficiency). The analysis results to the resultant extract are shown in Table 2 below.

3) Washing of TMP for Removing Alkali Metal Ion

The TMP-containing 2-ethylhexanol solution obtained from the step 2) was collected and fed into the bottom of a 7 L Scheibel-type multi-stage washing device at the rate of 100 g/min while deionized water for washing was fed continuously into the top of the multi-stage washing device at the rate of 8 g/min, thereby washing the TMP-containing 2-ethylhexanol solution to remove sodium ion present therein. The washing temperature was 60° C. As a washed resultant extract, TMP-containing 2-ethylhexanol solution was obtained through the top of the multi-stage washing device at the rate of 105.5 g/min. The content of sodium ion in the washed resultant extract was measured as 28 ppm by using an ion meter analyzer. The analysis results to the washed resultant extract are shown in Table 2 below.

TABLE 2

| Composition | Resultant mixture | (parts by weight) Washed resultant extract |
|---|---|---|
| Water | 3.8 | 6.8 |
| TMP | 21.6 | 17.7 |
| Lower boiling point material | 1.0 | 1.0 |
| Higher boiling point material | 1.6 | 1.6 |
| Sodium formate | 0.3 | 0.0 |
| 2-ethylhexanol | 71.8 | 72.9 |

4) Distillation and Recovery of Extraction Solvent and Purification of TMP

The washed resultant extract obtained from the step 3) was fed continuously into a supply end at the middle of a 15-stage Oldershaw distillation apparatus at the rate of 14.8 g/min to recover 2-ethylhexanol used as extraction solvent. The distillation conditions were the pressure of 200 mbar, the temperature of 130° C., and the reflux ratio of 0.5. A top effluent containing 99.5 weight % of 2-ethylhexanol was recovered through the top of the distillation apparatus at the rate of 12.3 g/min, and as a solvent-removed product, a bottom effluent containing 84.5 weight % of TMP was obtained through the bottom of the distillation apparatus.

Then, from the solvent-removed product, lower boiling point material was removed by using a 15-stage Oldershaw distillation apparatus, thereby obtaining a lower boiling point material-removed product. The conditions for removing lower boiling point material was the pressure of 200 mbar, the temperature of 131° C., and the reflux ratio of 2.0.

Then, from the lower boiling point material-removed product, higher boiling point material was removed by using a 5-stage Oldershaw distillation apparatus, thereby obtaining a final product of purified TMP (99.5 weight % of TMP). The conditions for removing higher boiling point material were the pressure of 5 mbar, the temperature of 223° C., and the reflux ratio of 2.0. During the purification of TMP, discoloration of TMP was not observed. The analysis results to the solvent-removed product, the lower boiling point material-removed product, and the final product of purified TMP are shown in Table 3 below.

TABLE 3

| Composition | Solvent-removed product | Lower boiling point material-removed product | (parts by weight) Final product of purified TMP |
|---|---|---|---|
| Water | 0.3 | 0.0 | 0.0 |
| TMP | 84.5 | 91.3 | 99.5 |
| Lower boiling point material | 3.9 | 0.2 | 0.3 |
| Higher boiling point material | 7.8 | 8.4 | 0.2 |
| Sodium formate | 0.0 | 0.0 | 0.0 |
| 2-ethylhexanol | 3.5 | 0.0 | 0.0 |

EXAMPLE 2

Purified TMP was prepared according to the same method as Example 1, except that 2-ethylhexanol was fed at the rate of 80 g/min in the step 2), and deionized water was fed at the rate of 10 g/min in the step 3). There was no loss of TMP during the extraction (100% of extraction efficiency), and the content of sodium ion in the washed resultant extract was measured as 17 ppm.

EXAMPLE 3

Purified TMP was prepared according to the same method as Example 1, except that 108.2 g (1.5 mol) of n-butylaldehyde (n-BAL) and 138 g of 48% aqueous solution of sodium hydroxide (1.7 mol of sodium hydroxide) were fed continuously for 105 minutes and 90 minutes, respectively, in the step 1). The resultant mixture of the TMP synthesis contained 181.7 g (1.4 mol) of TMP, which is an amount corresponding to 13.4 parts by weight to 100 parts by weight of the resultant mixture. There was no loss of TMP during the extraction (100% of extraction efficiency), and the content of sodium ion in the washed resultant extract was measured as 31 ppm.

COMPARATIVE EXAMPLE 1

In this Comparative Example, the extraction and washing of TMP were carried out simultaneously as follows.

The concentrated resultant mixture obtained from the step 1) of Example 1 was fed into the top of a 7 L Scheibel-type multi-stage extractor at the rate of 40 g/min while 2-ethylhexanol as extraction solvent was fed continuously into the bottom of the multi-stage extractor at the rate of 60 g/min. And, deionized water for washing was fed into the top of the multi-stage extractor at the rate of 3.2 g/min, thereby extracting and washing TMP simultaneously in a single step. At that time, the extractor's temperature was 60° C. As a resultant extract, TMP-containing 2-ethylhexanol solution was obtained through the top of the multi-stage extractor at the rate of 92.1 g/min. The extraction efficiency of TMP was as low as 97.4%, and the content of sodium ion in the washed resultant extract was measured as high as 4530 ppm.

COMPARATIVE EXAMPLE 2

In this Comparative Example, amyl alcohol having 5 carbons was used as extraction solvent as follows.

The concentrated resultant mixture obtained from the step 1) of Example 1 was fed into the top of a 7 L Scheibel-type multi-stage extractor at the rate of 40 g/min while amyl alcohol as extraction solvent was fed continuously into the bottom of the multi-stage extractor at the rate of 80 g/min, thereby extracting TMP. The extraction temperature was 60° C. As a resultant extract, TMP-containing amyl alcohol solution was obtained through the top of the multi-stage extractor at the rate of 94 g/min. The extraction efficiency of TMP was as low as 82%.

Then, the TMP-containing amyl alcohol solution was collected and fed into the bottom of a 7 L Scheibel-type multi-stage washing device at the rate of 80 g/min while deionized water for washing was fed continuously into the top of the multi-stage washing device at the rate of 44 g/min, thereby washing the TMP-containing amyl alcohol solution to remove sodium ion present therein. The washing temperature was 60° C. As a washed resultant extract, TMP-containing amyl alcohol solution was obtained through the top of the multi-stage washing device at the rate of 68 g/min. The content of sodium ion in the washed resultant extract was measured as high as 500 ppm.

INDUSTRIAL APPLICABILITY

As described above, according to the present invention, a separate formaldehyde recovery process may be omitted; the efficiency of TMP extraction can be maximized with using a relatively small amount of extraction solvent; the separation and recovery processes for extraction solvent can be simplified since a mixture of solvents is not used for TMP extraction; and the yield of TMP can be maximized while the amount of generated waste water can be minimized, thereby producing TMP economically in good efficiency.

The invention claimed is:

1. A method for preparing trimethylolpropane comprising the steps of:
   1) synthesizing trimethylolpropane by using n-butyl aldehyde, an aqueous solution of formaldehyde, and an aqueous solution of alkali metal hydroxide through aldol condensation reaction and Cannizzaro reaction;
   2) extracting trimethylolpropane from a resultant mixture of the step 1) by contacting the resultant mixture with an alcohol having 6 to 10 carbons;
   3) removing alkali metal ion from a resultant extract of the step 2) by contacting the resultant extract with water; and
   4) distilling the alkali metal ion-removed extract obtained from the step 3).

2. The method according to claim 1, wherein the aqueous solution of formaldehyde is fed earlier than the n-butyl aldehyde and the aqueous solution of alkali metal hydroxide into the reactor in the step 1).

3. The method according to claim 1, wherein the n-butyl aldehyde is fed into a reactor for 70 to 120 minutes in the step 1).

4. The method according to claim 1, wherein the aqueous solution of alkali metal hydroxide is fed into a reactor for 70 to 90 minutes in the step 1).

5. The method according to claim 1, wherein the amount of formaldehyde in the formaldehyde aqueous solution is 3 to 5 moles per mole of the n-butyl aldehyde in the step 1).

6. The method according to claim 1, wherein the alkali metal hydroxide is lithium hydroxide, sodium hydroxide, potassium hydroxide, or mixtures thereof in the step 1).

7. The method according to claim 1, wherein an organic acid is added to a resultant mixture of synthesis reactions in the step 1).

8. The method according to claim 7, wherein water is removed from the resultant mixture with added organic acid in the step 1).

9. The method according to claim 1, wherein the amount of alcohol having 6 to 10 carbons is 1 to 2 times the weight of the resultant mixture of the step 1) in the step 2).

10. The method according to claim 1, wherein the extraction is conducted at 30 to 80° C. for 30 to 90 minutes in the step 2).

11. The method according to claim 1, wherein the amount of water is 5 to 20 parts by weight to 100 parts by weight of the resultant extract of the step 2) in the step 3).

12. The method according to claim 1, wherein the removal is conducted at 30 to 80° C. for 30 to 90 minutes in the step 3).

13. The method according to claim 1, wherein the alkali metal ion-removed extract obtained from the step 3) contains alkali metal ions of 40 ppm or less.

14. The method according to claim 1, wherein the water used in the step 3) is recycled into the reactor in which the step 1) is conducted.

15. The method according to claim 1, wherein the alcohol having 6 to 10 carbons is recovered in the step 4) and is recycled into the step 2).

16. The method according to claim 1, wherein the alcohol having 6 to 10 carbons is distilled, and then lower boiling point material and higher boiling point material are removed sequentially by distillation, in the step 4).

17. The method according to claim 1, wherein the alcohol used as extraction solvent is an alcohol having 8 carbons in the step 2).

* * * * *